(12) United States Patent
Parkkinen

(10) Patent No.: US 8,568,815 B2
(45) Date of Patent: Oct. 29, 2013

(54) SOLUBLE COMPLEXES OF CURCUMIN

(75) Inventor: Jaakko Parkkinen, Espoo (FI)

(73) Assignee: Novobion Oy, Espoo (FI)

( * ) Notice: Subject to any disclaimer, the term of this patent is extended or adjusted under 35 U.S.C. 154(b) by 369 days.

(21) Appl. No.: 12/857,122

(22) Filed: Aug. 16, 2010

(65) Prior Publication Data

US 2011/0034564 A1    Feb. 10, 2011

Related U.S. Application Data

(63) Continuation-in-part of application No. PCT/FI2009/050119, filed on Feb. 16, 2009.

(60) Provisional application No. 61/029,037, filed on Feb. 15, 2008.

(51) Int. Cl.
*C09B 61/00* (2006.01)
*A61K 36/9066* (2006.01)

(52) U.S. Cl.
USPC ............. 426/540; 514/58; 514/679; 536/103; 426/250; 426/588

(58) Field of Classification Search
USPC .................... 426/250, 540, 588; 514/58, 679; 536/103; 435/1.2
See application file for complete search history.

(56) References Cited

U.S. PATENT DOCUMENTS

| | | | |
|---|---|---|---|
| 4,999,205 A * | 3/1991 | Todd, Jr. ..................... | 426/250 |
| 2007/0155695 A1 | 7/2007 | Wirth et al. | |

FOREIGN PATENT DOCUMENTS

| | | | |
|---|---|---|---|
| CN | 1543933 A | | 11/2004 |
| DE | 10233598 | * | 7/2002 |
| DE | 10233598 A1 | | 2/2004 |
| JP | 2006111534 A | | 4/2006 |
| WO | 95/18606 A1 | | 7/1995 |
| WO | 2004/010941 A2 | | 2/2004 |
| WO | 2004/087121 A2 | | 10/2004 |

OTHER PUBLICATIONS

"American Thoracic Society/European Respiratory Society International Multidisciplinary Consensus Classification of the Idiopathic Interstitial Pneumonias", American Journal of Respiratory and Critical Care Medicine, 2002, pp. 277-304, vol. 165.
Baglole et al., "Fluorescence Enhancement of curcumin upon inclusion into parent and modified cyclodextrins." Journal of Photochemistry and Photobiology A: Chemistry, May 10, 2005, pp. 230-237, vol. 173.
Chen et al. "Curcumin Has Potent Liver Preservation Properties in an Isolated Perfusion Model", Experimental Transplantation, Oct. 15, 2006, pp. 931-937, vol. 82, No. 7.

(Continued)

*Primary Examiner* — Savitha Rao
(74) *Attorney, Agent, or Firm* — Sughrue Mion, PLLC

(57) ABSTRACT

A composition comprising a water-soluble and stable complex formed by an alkyl ether derivative of gamma-cyclodextrin and curcumin and optionally comprising non-complexed cyclodextrin, the molar ratio of curcumin to cyclodextrin being between 1:1 and 1:6, and a method of manufacturing such a composition. The water-soluble and stable complex of curcumin is useful in therapy, e.g. for treatment of cancer, leukemia, myocardial infarction, stroke, sepsis, acute lung injury, acute liver failure, acute tubular necrosis, acute pancreatitis, radiation injury and other life-threatening conditions in a human or animal subject, as well as for preserving human or animal organs, tissues or cells at a hypothermic temperature.

6 Claims, 2 Drawing Sheets

Effect of pH during contacting of curcumin with the cyclodextrin on curcumin recovery in the complex

(56) References Cited

OTHER PUBLICATIONS

Shrimm, R.C. "Turmeric: a brief review of medicinal properties", Fitoterapia, 1997, pp. 483-493, vol. LXVIII, No. 6.

Tonnesen, et al. "Studies of curcumin and curcuminoids. XXVII. Cyclodextrin complexation: solubility, chemical and photochemical stability", International Journal of Pharmaceutics, 2002, pp. 127-135, vol. 244.

* cited by examiner

SOLUBLE COMPLEXES OF CURCUMIN

CROSS REFERENCE TO RELATED APPLICATIONS

This application is a Continuation-In-Part of Application No. PCT/FI2009/050119 filed Feb. 16, 2009, claiming priority based on U.S. Provisional Patent Application No. 61/029,037, filed Feb. 15, 2008, the contents of all of which are incorporated herein by reference in their entirety.

BACKGROUND OF THE INVENTION

1. Field of the Invention

The present invention relates to water-soluble curcumin complexes. In particular, the invention concerns aqueous compositions containing water-soluble and stable curcumin complexes. The invention also concerns methods of solubilizing curcumin by forming stable cyclodextrin complexes. Further, the present invention relates to medical, pharmaceutical and nutraceutical formulations of curcumin and a composition and methods of protecting cells and organs.

2. Description of Related Art

Curcumin, chemically called diferuloylmethane, is a hydrophobic polyphenol derived from the rhizome of the perennial herb *Curcuma longa*. It has a wide spectrum of biological and pharmacological activities. Curcumin isolated from turmeric powder contains two other curcuminoids, demethoxycurcumin and bisdemethoxycurcumin, which differ in their biological activities. Curcumin is the most active curcuminoid in most in vitro bioassays but even the other curcuminoids have proven effective in some disease models.

Curcumin has been shown to exhibit potent anti-inflammatory, immunomodulatory, antiproliferative and anticarcinogenic activities and protect cells and tissues against various injury mechanisms. A number of preclinical studies have indicated that curcumin is a promising therapeutic agent for several diseases and clinical conditions, including, for example, the treatment of cancer and leukemias, stroke, myocardial infarction, rheumatoid arthritis, inflammatory bowel disease, pancreatitis, sepsis, hemorrhagic shock, organ transplantations, and radiation injury.

Several molecular targets have been identified for curcumin, and the interactions of curcumin with these targets explain at least part of the therapeutic effects identified in animal disease models. Furthermore, curcumin has proved to be remarkably safe in animal studies and phase I clinical trials even at high dose levels.

The major problem limiting the exploitation of curcumin's potentially valuable therapeutic effects is its low bioavailability. In practice, only very low or undetectable levels of curcumin can be achieved in blood by oral administration of curcumin (1). The low bioavailability of curcumin has so far limited its medical use.

The main reasons contributing to the low bioavailability of curcumin are its very low aqueous solubility and rapid intestinal metabolism, particularly in human subjects. Furthermore, the low aqueous solubility and poor stability of curcumin have hindered the development of pharmaceutical formulations suitable for parenteral and mucosal administration, which would lead to effective concentrations of curcumin in tissues.

Various methods have been tried to enhance curcumin delivery, including its incorporation into liposomes and nanoparticles. So far these formulations have not been shown to deliver effective concentrations of curcumin into tissues or to enable the treatment of diseases and injuries affecting organs like the brain, lungs, kidney, liver or bladder.

A few publications have addressed interactions of curcumin with cyclodextrins (2,3,4). Cyclodextrins are cyclic oligosaccharides consisting of $\alpha(1\text{-}4)$-linked glucopyranose units, which form a lipophilic cavity and a hydrophilic outer surface. Their apolar cavity is able to include hydrophobic molecules by non-covalent forces and thereby improve their water solubility. However, the reported experiments suggest that only low concentrations of curcumin can be solubilized even with a high molar excess of cyclodextrins. The hydrolytic stability of curcumin in these complexes was improved but still short-term, and photostability of curcumin was impaired as compared to curcumin dissolved in methanol (2,4). Due to the low concentration and limited stability of curcumin and the high excess of cyclodextrins required, these preparations are not suitable for therapeutic use. These complexes were formed by contacting curcumin with cyclodextrin under neutral or slightly acidic conditions.

DE Patent Application No. 10233598 describes cosmetic or dermatological compositions containing curcumin and cyclodextrins. However, it is not demonstrated that the described compositions would contain curcumin in water-soluble form and the examples of the application describe only oil in water emulsions, which are not suitable for parenteral administration.

U.S. Pat. No. 5,702,881 to Brasile describes the addition of cyclodextrin to a preservation solution of organs intended for transplantation. The addition of curcumin dissolved in dimethyl sulfoxide to a preservation solution of organ transplants has also been described in the prior art (5). U.S. Patent Application No. 20090123904 further describes the addition of a positively charged cyclodextrin to organ preservation solution, preferentially combined with antioxidants resveratrol or curcumine. However, these compositions do not enable the delivery of curcumin into organ transplants at such concentrations, which would effectively protect ischemically damaged organ transplants against reperfusion injury.

The present invention seeks to alleviate the problems associated with curcumin administration by seeking novel methods to solubilize curcumin in concentrations high enough to allow administration in effective doses to human and animal subjects. Further, the present invention seeks to provide stable water-soluble formulations and compositions of curcumin which make possible the delivery of effective concentrations of curcumin into organs and tissues. The present invention also seeks to provide for the manufacture of pharmaceutical and nutraceutical formulations of curcumin. Finally, the present invention also seeks to provide compositions and methods for the protection of organs and cells.

SUMMARY OF THE INVENTION

It is an aim of the invention to provide novel water-soluble and stable compositions of curcumin.

It is a second aim of the invention to provide a method of manufacturing novel cyclodextrin complexes of curcumin.

It is a third aim of the invention to provide a method of manufacturing water-soluble and stable composition of curcumin.

It is a fourth aim of the invention to provide novel pharmaceutical compositions of curcumin, which can be administered to human and animal subjects at effective doses for the treatment of various diseases and clinical conditions.

It is a fifth aim of the present invention to provide novel compositions and methods for protection of cells, tissues and organs during hypothermic preservation, perfusion, and reperfusion.

It is still a sixth aim of the present invention to provide novel, endotoxin-free compositions of curcumin, in particular in complexes with cyclodextrins.

The present invention is based on the unexpected finding that it is possible to dissolve curcumin at high concentrations in an alkaline aqueous solution containing a chemically modified derivative of γ-cyclodextrin. By lowering the pH of the aqueous solution below 8 a cyclodextrin complex of curcumin is obtained which is stable in the aqueous solution.

The cyclodextrin complex obtainable by the present invention is soluble at much higher curcumin concentrations in aqueous solutions than previously described cyclodextrin complexes or other curcumin formulations, and the molar excess of cyclodextrin required for solubilization of curcumin is clearly lower than previously described. Curcumin is also remarkably stable in the described complex and has much better stability, in particular hydrolytic and photochemical stability, than in the previously described complexes.

The cyclodextrin complex of curcumin can be formulated to pharmaceutical compositions suitable for administration through different parenteral and mucosal routes, orally and topically to human or animal subjects. Importantly, the new curcumin formulations enable efficient delivery of curcumin to target organs and tissues at effective tissue concentrations for treatment of various diseases and clinical conditions, including mild, moderate and severe conditions and diseases.

The solution composition of curcumin can be also added to preservation and perfusion solutions of organs, tissues and cells ex vivo whereby it leads to protective concentrations of curcumin in cells and tissues. Further, the complex can be used for the manufacture of nutraceutical preparations containing curcumin.

The method according to the present invention of manufacturing an endotoxin-free formulation of curcumin comprises, generally, the steps of contacting curcumin with cyclodextrin, in particular gamma-cyclodextrin, in an aqueous phase at a pH of at least 11 to form a solution of curcumin and cyclodextrin, lowering the pH of said solution to below pH 8, and recovering the solution thus obtained containing an endotoxin-free cyclodextrin complex of curcumin, said complex being dissolved in the aqueous phase. In particular the method may comprise dissolving curcumin at a pH of at least 11 to form a solution, lowering the pH of the solution to below pH 8 in the presence of a complexing agent, such as cyclodextrin or albumin, and recovering the solution thus obtained.

By the present uncomplicated method, endotoxins can be efficiently removed from the biological raw materials used.

DETAILED DESCRIPTION OF PREFERRED EMBODIMENTS

Figure 1:
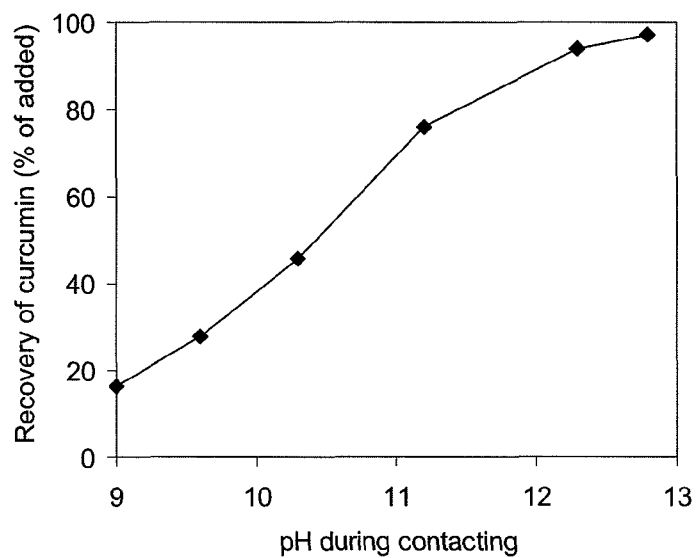
FIG. 1 shows the effect of pH (in a pH range from 9 to 13) during contacting of curcumin with cyclodextrin during manufacturing of the complex. 2-Hydroxypropyl-γ-cyclodextrin was dissolved at 150 g/l in 1-200 mmol/l sodium hydroxide solutions, and curcumin was added to a concentration of 11.7 g/l. The solutions were agitated for 10 min, pH was measured and adjusted to 7.0 with 0.5 mol/l hydrochloric acid. Curcumin concentration was determined by HPLC and absorbance at 430 nm.
Figure 2:
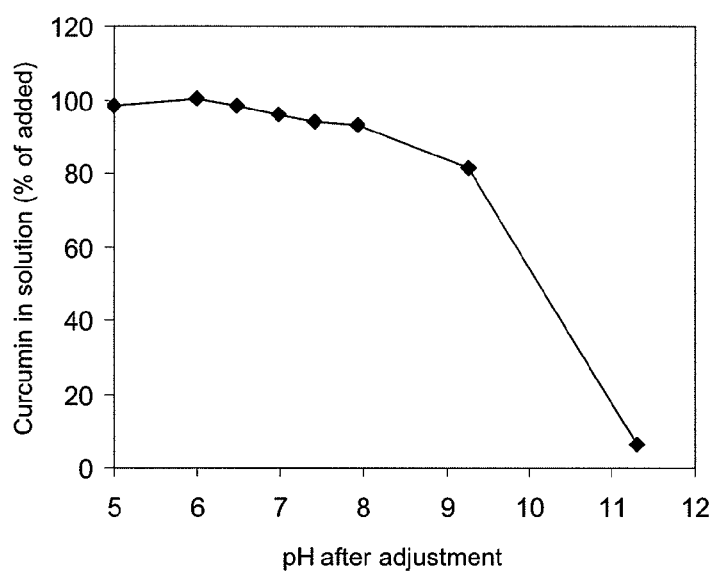
FIG. 2 shows the effect of lowering the pH on the stability of the cyclodextrin complex of curcumin. Curcumin (8.8 g/l) was dissolved in 0.1 mol/l sodium hydroxide containing 2.7 fold molar excess of 2-hydroxypropyl-γ-cyclodextrin and the solution was adjusted to different pH values between pH 5.0 and pH 11.3 with citric acid. The solutions were stored for 7 days at 23° C. protected from light, after which the concentration of curcumin was determined by HPLC.

Suitable cyclodextrins for the manufacture of a cyclodextrin complex of the present invention are ether and alkyl derivatives of γ-cyclodextrin. In particular the derivatives are (substituted)alkyl ether derivatives of γ-cyclodextrin, wherein the alkyl group is branched or linear and comprises 1 to 6 carbon atoms. Preferably the alkyl group is substituted with 1 to 3 substituents selected from the group consisting of hydroxy, sulfoxy, amino and thio groups. As examples of suitable ethers, hydroxyalkyl and sulfoalkyl ether derivatives can be particularly mentioned.

According to one embodiment, the hydroxyalkyl group is hydroxypropyl, for example 2-hydroxypropyl, dihydroxypropyl or hydroxyethyl and the sulfoalkyl group is sulfobutyl.

The degree of substitution (DS) of the cyclodextrin ether is typically 3-10. The degree of substitution as used here means the average number of etherifying groups, such as hydroxyalkyl or sulfoalkyl groups, per cyclodextrin molecule.

The γ-cyclodextrin may also contain alkyl substituents, such as lower alkyl groups, e.g. methyl or ethyl groups. Glucosyl and maltosyl derivatives of γ-cyclodextrin may be also used.

According to a specific embodiment the cyclodextrin is a 2-hydroxypropyl-γ-cyclodextrin with a substitution degree of 3 to 7. 2-Hydroxypropyl-γ-cyclodextrin suitable for the manufacturing of the curcumin complex is supplied by Wacker Chemie AG, Munich, Germany, under the tradename "CAVASOL W8 Pharma".

The cyclodextrin complex can contain other curcuminoids than curcumin. A curcuminoid composition similar to the naturally occurring composition in turmeric powder is suitable. Commercially available curcumin preparations obtained by extraction of turmeric powder contain 95% or more curcuminoids of which about 70-80% is curcumin, 15-25% demethoxycurcumin and 3-7% bisdemethoxycurcumin.

Any of the curcuminoids can be used in pure form. Synthetic curcuminoids can be also used. As used hereafter, by "curcumin" it is meant preferably curcumin, demethoxycurcumin and bisdemethoxycurcumin, and mixtures thereof.

In a preferred embodiment, the cyclodextrin complex of curcumin is an inclusion complex.

Methods for the isolation of curcumin from turmeric powder have been described for example in U.S. Pat. No. 5,861, 415. Curcumin and other curcuminoids may be further purified, for example by chromatography. In one embodiment, the use of silica gel 60 is described.

With "water-soluble" it is meant that the cyclodextrin complex of curcumin is soluble at a curcumin concentration of at least 10 mmol/l in aqueous solutions without precipitation. The complex is typically also "stable" which means that the concentration of curcumin in the complex decreases less than 20% during storage for three months at room temperature (23±2° C.) or during storage for twelve months at 2 to 8° C., when protected from light. Preferably the composition is stable for 12 months at 2-8° C. or below 25° C.

The complex is manufactured by contacting curcumin with the cyclodextrin in an alkaline aqueous solution at a pH of at least pH 11, preferentially at least pH 12. A suitable alkaline solution is for example 0.1-0.5 mol/l sodium hydroxide. Using such a concentration a pH in the preferred range of 11 to about 14 can be reached. Potassium hydroxide and other strong bases, as well as various alkali metal carbonates and earth alkaline metal hydroxides and carbonates, can also be used. Mixtures of alkaline compounds can, naturally, also be employed.

A cyclodextrin concentration of 10-250 g/l is suitable, but higher concentrations may be used. Curcumin is added at a molar ratio from 1:1 to 1:6 to cyclodextrin, and the solution is agitated. The solution is protected from light during manufacturing to prevent curcumin degradation. The pH is adjusted to below 8, but not less than about 3, in particular to about 4.0-7.6.

The pH can be adjusted, for example, with hydrochloric, phosphoric acid or organic acids, such as citric acid, lactic acid, malic acid, tartaric acid, acetic acid, gluconic acid, succinic acid, and combinations thereof. A suitable combination is for example to use hydrochloric acid and a hydroxy acid, such citric acid, in which case the complex can be recovered in a solution composition containing sodium chloride and optionally sodium citrate at a pH and osmolarity suitable for intravenous infusion.

Some precipitate may be formed during pH adjustment depending on the conditions used. Such precipitate can be removed by filtration.

Further adjustments of the composition can be made and other auxiliary substances may be added, such as tonicity modifiers, complexation-enhanging agents, stabilizers, and cryoprotectants, examples of which are given below. The composition can be sterile filtered.

The curcumin complex can be recovered from the solution or it can be subjected to further processing in solution without isolation.

During the manufacturing of the complex, curcumin and cyclodextrin can be contacted in different ways. A first method comprises the steps of making an alkaline cyclodextrin solution with a pH of at least pH 11, mixing curcumin with the alkaline cyclodextrin solution and, after dissolution, lowering the pH to below pH 8. This is a preferred method. Curcumin typically dissolves in a few minutes.

The alkaline cyclodextrin solution is preferably produced by dissolving the cyclodextrin in water, for example at essentially neutral conditions, and then adding an alkaline agent to increase the pH. For the preparation of the aqueous solution of the cyclodextrin, non-ionic water (e.g. water for injection having a low conductivity) is preferably employed. The cyclodextrin can be relieved from contaminants by filtration, for example by using a positively charged membrane or filter, or by chromatography, such as ion-exchange or affinity chromatography.

In a second method curcumin is first dissolved in alkaline solution at a pH of at least pH 11, the cyclodextrin is mixed with the alkaline curcumin solution, and after dissolution, the pH is lowered.

A third method comprises the steps of dissolving curcumin in an alkaline solution at a pH of at least 11, dissolving the cyclodextrin in a second solution, mixing the solutions, and lowering the pH.

In all of the above embodiments, curcumin used in a solid form can be wetted and degassed before mixing with the cyclodextrin solution.

An organic solvent, such as ethanol may be added to enhance the solubility of curcumin.

A suitable temperature for the contacting step is 2-40° C. In one embodiment, the temperature is about 15 to 30° C., in particular 20 to 25° C.; in another embodiment, the temperature, is 20-30° C. Thus, it is possible to act at room temperature or somewhat below or above.

Mixing of the components in the contacting step can be effected by any conventional mixing, agitating or blending apparatus. Thus, the term "mixing" as used herein includes all conditions under laminar or turbulent conditions wherein the components are mixed together. Preferably various industrial or laboratory agitators or blenders or mixers are used. Such equipment include paddle mixers and rotor stator mixers. High shear conditions will particularly promote the mixing of the components.

Cyclodextrins and other biological raw materials typically contain bacterial endotoxins due to the microbial enzymes used in the production processes. Surprisingly, it was found that when curcumin was dissolved by the method of the present invention, in particular using the embodiment described in Example 1, a curcumin complex with less than 1 IU/ml endotoxins was obtained even when a commercial cyclodextrin was used, which contained about 100 IU/ml endotoxins when dissolved in pyrogen-free water at 100 g/l.

Thus, the method of the present invention is particularly beneficial in the manufacture of endotoxin-free curcumin complexes (and similar cyclodextrin complexes of drug molecules) by eliminating endotoxins present in the biological starting materials used.

The recovered cyclodextrin complex of curcumin is stable in an aqueous solution composition for at least three months at room temperature. The concentration of the complex influences its stability in solution so that dilute solutions are less stable. It is therefore preferable to have a solution composition with a curcumin concentration of more than 1 mmol/l and up to about 100 mmol/l, preferentially at least 5 mmol/l. A practical curcumin concentration is at least 10 mmol/l, such as 10-60 mmol/l.

The complex can be concentrated and diafiltered by ultrafiltration by using membranes with a molecular weight cut-off value of about 10 kDa or lower.

The complex can be dried, for example by lyophilization, spray-drying, spray-freeze-drying, antisolvent precipitation, a process utilizing a supercritical or near supercritical fluid, or other methods known to those of ordinary skill in the art to make a powder, granular or other solid form.

The complex, or more precisely the composition, according to the present invention has an intense red color at neutral pH (pH of about 6.8 to 7.5, in particular about 7.4). Preferably the red colour is detectable at a curcumin concentration of 10 mmol/l or more. This differentiates the composition from previously described curcumin compositions, which are orange or yellow at neutral pH.

The finding that it is possible to obtain a water-soluble and stable cyclodextrin complex with an excellent yield of curcumin using alkaline pH was surprising as in the prior art it has been considered that curcumin is rapidly hydrolyzed at alkaline pH (6). U.S. Pat. No. 4,999,205 describes a method for the manufacture of clear water-soluble curcumin complexes with improved light stability and tinctorial power. The method includes the steps of contacting a substrate and curcumin in an aqueous solution at a pH above 9, at which curcumin is present in its water-soluble red alkaline form, and then acidifying to drop the pH to below about 8, thereby complexing the curcumin in its neutral yellow form with the substrate. The stability of curcumin was determined by absorption; however, it has been shown that the hydrolytic degradation products of curcumin have a similar absorption as curcumin making absorption an unreliable method for stability assessment of curcumin (6). In the present invention a reverse phase HPLC method is used for the determination of curcumin concentrations.

U.S. Pat. No. 4,999,205 mentions as substrates for curcumin complex formation water-soluble branched chain or cyclic polysaccharide and water-soluble or water-dispersible proteins. Cyclodextrins generally are mentioned as a substrate. In our comparative studies described in Example 2, we prepared a curcumin complex with gelatin essentially as described in U.S. Pat. No. 4,999,205. We also prepared curcumin complexes with non-derivatized γ-cyclodextrins and ether derivatives of β-cyclodextrin under different conditions, including the conditions of the present invention. A considerable proportion of curcumin precipitated during lowering of the pH or storage of the other cyclodextrin complexes and the gelatin complex, and only low concentrations of soluble curcumin was obtained. The recovery of the added curcumin varied from less than 1% to 26% when other cyclodextrins were used, whereas more than 95% of curcumin was recovered in the cyclodextrin complex of the present invention. Water-soluble complexes with the other cyclodextrins were obtained only in the presence of clearly higher molar ratio of cyclodextrin to curcumin than with the complex of the present invention. Furthermore, the other complexes were not stable during storage.

DE Patent Application No. 10233598 describes cosmetic or dermatological compositions containing curcumin and cyclodextrins, and in Example 2, an oil in water emulsion (creme) containing curcumin and hydroxypropyl-γ-cyclodextrin is mentioned. The method of the manufacturing and the pH of the compositions are not described. From the scientific publications (2,3,4) and from our own experiments it is evident that curcumin does not form a water-soluble complex when it is contacted with hydroxypropyl-γ-cyclodextrin at the mass ratios described in the DE 10233598 and at a pH which could be used for dermatological compositions (pH 3-9). Instead, curcumin may be dissolved in the oil phase of the described compositions, which are not suitable for parenteral administration, unlike the compositions of the present invention.

When curcumin powder was mixed in an aqueous solution of hydroxypropyl-γ-cyclodextrin at neutral or slightly acidic pH similarly as described in the prior art (2,3,4), only a low concentration (0.5 mmol/l) of soluble curcumin was obtained (Example 5). Furthermore, the proportion of bisdemethoxy curcumin was clearly higher and the proportion of curcumin lower in the solution than in the curcumin powder. In contrast, curcumin concentrations above 50 mmol/l can be obtained by the present method and the curcuminoid composition is similar as in the curcumin powder.

The hydrolytic and photochemical stability of curcumin is greatly enhanced in the cyclodextrin complex prepared by the present method. A sterile solution of cyclodextrin curcumin obtained by the present method has been stable for 2 years at 2-8° C. and even at 21-25° C. the change in curcumin concentration was less than 20% after 2 years (Experiment 5). This is much longer than the described stability (half life>100 hours) of the most stable cyclodextrin complexes of curcumin described in the prior art (4). Furthermore, the photochemical stability of curcumin is much higher than that of curcumin dissolved in methanol, whereas the cyclodextrin complexes described in the prior art have lower photostability than curcumin in methanol.

It is therefore evident that the cyclodextrin complex of curcumin according to the present invention is superior to the other cyclodextrin complexes and compositions of curcumin known in the prior art. First, the novel complex is soluble at much higher curcumin concentrations. Second, only a low molar excess of cyclodextrin is required for the formation of the complex, which is important because cyclodextrins may cause adverse effects when administered at high doses. Third, the present complex has much higher stability, in particular hydrolytic and photochemical stability, than the complexes described in the prior art. Fourth, a curcumin composition with a natural curcuminoid composition can be prepared by the novel method. Finally, the complex is essentially free of endotoxins. These properties are important for the pharmaceutical and other medical and nutraceutical uses of the complex.

The present invention provides pharmaceutical compositions for the prevention and treatment of diseases and clinical conditions, in which curcumin has therapeutic efficacy. The compositions contain an effective amount of the cyclodextrin complex of curcumin together with auxiliary substances.

In many diseases, particularly in life-threatening conditions, it is necessary to give curcumin as an intravenous injection or infusion or through other parenteral routes to achieve therapeutic concentrations in critical tissues. A suitable formulation is at simplest the solution composition obtained after manufacturing of the cyclodextrin complex, when a sterile aqueous solution is manufactured using methods and conditions known to those with ordinary skill in the art. The solution composition contains at least one tonicity modifier, such as sodium chloride, and optionally a buffer. The buffer is preferentially a hydroxy acid or a salt thereof, such as citrate, lactate, malate, tartrate or gluconate.

Other auxiliary substances may be added, such as tonicity modifiers, complexation-enhancing agents, stabilizers, preservatives, antioxidants, chelating agents, and cryoprotectants. The osmolarity of the solution is preferentially 240-600 mOsmol/l and pH is at least about 4 and below 8, preferentially 4.0-7.6. The formulation may be filled aseptically into injection or infusion bottles, ampoules, bags, or syringes. It may be freeze-dried and stored in powder form until reconstitution before administration.

The formulation may be administered through different parenteral routes, such as intravenously, intravascularly, intra-arterially, subcutaneously, intramuscularly, intra-articularly, intraperitoneally, or intrathecally.

By the novel method a pharmaceutical curcumin formulation containing for example 20 mg/ml curcumin can be manufactured (Example 4). This makes it possible to administer as an intravenous infusion doses as high as 100 mg/kg in a feasible infusion volume, such as 350 ml to a 70-kg patient.

The cyclodextrin complex of curcumin can be also used for the manufacture of colloidal drug carrier systems of curcumin, such as liposomes and polymer based nanoparticles and microparticles. Particularly, the cyclodextrin complex of curcumin can be entrapped into liposomes, such as pegylated liposomes, for prolonged half-life in circulation and more efficient targeting to tumors. The use of the cyclodextrin complex of curcumin results in the entrapment of curcumin in the aqueous space inside the liposomes, and higher curcumin concentrations and improved stability may be obtained.

A further application of the cyclodextrin complex of curcumin is the manufacture of pharmaceutical formulations for inhalation. The aqueous composition according to the present invention is suitable for aerosolization and the resulting droplet-size is compatible with pulmonary deposition. Aerosol can be generated by ultrasonic or pneumatic nebulizer for efficient delivery of curcumin into the lungs. As shown in Experiment 6, delivery of curcumin into the lungs by nebulization of the present solution composition effectively mitigates inflammatory and fibrotic lung disorders. An aqueous formulation for aerolization contains similar auxiliary substances as the solution for intravenous administration, and the concentration of the cyclodextrin complex is adjusted to an optimal concentration for aerolization. Curcumin concentration is preferentially at least 5 mmol/l. The cyclodextrin complex can also be used for the manufacture of an inhalation powder for administration of curcumin by a powder inhalation device or by a metered-dose inhaler in a suitable formulation. Pulmonary dosing not only results in effective concentrations of curcumin in the lungs but may be also used for systemic delivery of curcumin.

A further therapeutic application of the present formulation is intravesical administration for the treatment of urothelial cell carcinoma and other disorders of the urinary bladder. Instillation of the present composition intravesically results in efficient delivery of curcumin into the urothelium, as demonstrated in Example 7. Curcumin has potent antitumor activity of its own and it has been shown to enhance the efficacy of chemotherapy and prevent resistance formation against chemotherapy and biological treatments of bladder cancer. A solution composition according to the present invention is diluted before intravesical instillation with a diluent to the effective concentration. A suitable curcumin concentration for intravesical instillation is 10-1000 μmol/l, preferentially 30-600 μmol/l. A powder formulation may be also used, which is reconstituted before use with the diluent. As an example, the diluent can be 0.9% sodium chloride solution.

A further therapeutic application of the novel pharmaceutical composition is brain targeting by intranasal delivery. Curcumin has proven effective in the treatment of neuroinflammatory and neurodegenerative diseases, brain tumors and stroke in animal models but currently there is no clinically approved method for curcumin targeting into the brain. It is generally known that the nerve cells of the olfactory epithelium in the roof of the nasal cavity traverse into the olfactory bulb of the brain, which provides a potential route for drug delivery into the brain. When administered intranasally, the present composition effectively delivers curcumin through the olfactory epithelium and further to the brain tissue, bypassing the blood brain barrier (Example 8). Effective concentrations of curcumin are detectable in brain already 30 min after intranasal application. The present composition can be given as nasal drop, spray or aerosol, or other suitable nasal formulation.

The present invention also provides pharmaceutical and nutraceutical compositions for oral administration of curcumin in the dosage form of oral solution, a tablet, a caplet, a pellet, a capsule, a granule, a pill, a powder or a sachet. The present invention further provides pharmaceutical compositions for topical administration of curcumin to skin and mucosal surfaces, including oral, gastroenteral, nasal, vaginal and rectal mucosae, eyes and ears, and for transmucosal delivery. The pharmaceutical form can be cream, gel, lotion, solution, suspension, spray, aerosol, ointment, paste, powder, granular form or transdermal patch. It can be liquid, semisolid or solid, and it can be mucoadhesive or bioadhesive. A buccal or nasal delivery system or a suppository for rectal administration can be manufactured. These pharmaceutical formulations contain the cyclodextrin complex of curcumin as an active ingredient together with auxiliary substances (excipients) depending on the dosage form. The choice of the excipients can be made based on the intended route of administration and pharmaceutical practice. The excipients may include solubility and complexation-enhancing agents, solvents, fillers, vehicles, coatings, disintegrants, flavorants, binders, buffers, chelating agents, foam control agents, emollients, humectants, lubricants, plasticizers, preservatives, antioxidants, thickeners, mucolytic, mucoadhesive or bioadhesive substances, or a combination thereof.

A complexation-enhancing agent can be added to enhance the complexation of curcumin with the cyclodextrin. Suitable complexation enhancing agents include one or more pharmacologically inert water soluble polymers, hydroxy acids, and other organic compounds typically used in liquid formulations to enhance the complexation of a particular agent with cyclodextrins. Water soluble natural polymers include polysaccharides such as inulin, pectins, algin derivatives and agar, and polypeptides such as casein and gelatin. Suitable water soluble semi-synthetic polymers include cellulose derivatives, such as methylcellulose, carboxymethylcellulose, hydroxyethyl cellulose, hydroxypropyl cellulose, hydroxypropyl methylcellulose, hydroxyethyl ethylcellulose, hydroxypropyl ethylcellulose, and hydroxypropyl methylcellulose phthalate. Suitable water soluble synthetic polymers include polyoxyethylene derivatives, such as polyethylene glycols and polyvinyl derivatives, such polyvinyl alcohol, polyvinylpyrrolidone and polystyrene sulfonate, and various copolymers of acrylic acid, such as carbomer. Suitable hydroxy acids include citric acid, malic acid, lactic acid, and tartaric acid and others known to those of ordinary skill in the art.

Buffering agents include, by way of example and without limitation, the following acids and their sodium and potassium salts: acetic acid, adipic acid, citric acid, maleic acid, lactic acid, tartaric acid, fumaric acid, succinic acid, phosphoric acid, and gluconic acid. Suitable tonicity modifiers include for example glycerol, lactose, mannitol, dextrose, sodium chloride, sorbitol, sucrose and trehalose. Stabilizing agents include, for example, albumin, glycine and other amino acids, glycerol, mannitol, polyethylene glycol, propylene glycol, sucrose and others known to those of ordinary skill in the art. Preservatives, antioxidants and chelating agents include, for example, benzoic acid, benzyl alcohol, chlorhexidine gluconate, chlorobutanol, edetate (EDTA), pentetate, phenylethyl alcohol, sorbic acid, methyl, ethyl and propyl parabens, ascorbic acid, ascorbyl palmitate, retinyl palmitate, butylated hydroxyanisole, butylated hydroxytoluene, monothioglycerol, and propyl gallate. Cryoprotectants include for example glycerol, trehalose, propylene glycol, and polyethylene glycol.

Solubilizing agents include, by way of example and without limitation, alginic acid, carboxymethylcellulose, cellulose, glycerol, ethylene glycol, and propylene glycol. Suitable fillers include for example calcium carbonate, dibasic calcium phosphate, lactose, magnesium carbonate, magnesium oxide, lactose anhydrous, microcrystalline cellulose and mannitol. Examples of suitable binders include alginic acid, methylcellulose, and polyvinylpyrrolidone. Suitable lubricants are for example stearic acid, talc, sodium stearyl fumarate, glyceryl behenate, magnesium silicate, magnesium trisilicate and hydrogenated castor oil, and a mixture thereof. As the disintegrator, there are mentioned, for example, croscarmellose codium, crospovidone, starch, sodium starch glycolate, carboxymethyl cellulose, and microcrystalline cellulose. A glident can be for example colloidal anhydrous silica and talc. As coating agents, there are mentioned, for example, carboxymethylcellulose, copovidone, titanium dioxide.

It is obvious that many auxiliary substances or excipients serve more than one function and many other substances not mentioned here are known to those of ordinary skill in the art and can be used in the formulations of the present invention.

Diseases and clinical conditions, which can be treated with the pharmaceutical formulations containing the cyclodextrin complex of the present invention, include various forms of cancer and leukemias, cardiovascular diseases such as myocardial infarction, stroke, sepsis, acute lung injury, which as used herein comprises acute respiratory distress syndrome, acute liver failure, acute tubular necrosis, acute pancreatitis, graft versus host disease and graft rejection, and radiation injury of different organs. Further clinical conditions include, but are not limited to, autoimmune diseases and inflammatory diseases such as rheumatoid arthritis, vasculitis and connective tissue disorders, inflammatory bowel diseases, nephropathies, hepatitis, liver injury and fibrosis, skin diseases such as psoriasis, scleroderma and skin cancers, lung injury and fibrosis, which as used herein comprises idiopathic pulmonary fibrosis and the other interstitial lung diseases according to the consensus classification of American Thoracic Society/European Respiratory Society (7), chronic obstructive pulmonary disease, asthma, cystic fibrosis, neurodegenerative and neuroinflammatory diseases of the central nervous system such as Parkinson's disease, Alzheimer's disease and multiple sclerosis. Brain tumors, including gliomas, medulloblastoma and neuroblastoma can also be treated.

The pharmaceutical compositions of the present invention can be further used for treatment or reduction of oral and gastrointestinal mucositis in a patient undergoing or preparing to undergo chemotherapy or radiotherapy The pharmaceutical formulations of the present invention can be further used in the prevention and treatment of ischemia/reperfusion injury, which takes place in clinical conditions characterized by temporary decrease or complete stop of blood flow to one or several organs (ischemia) followed by restoration of blood flow (reperfusion). These clinical conditions include organ transplantations, thrombolytic therapy and other revascularization procedures, cardiovascular surgery such as cardiac surgery with or without cardiopulmonary bypass and angioplastic surgery, hemorrhagic shock and other forms of shock. The present composition also has significant antimicrobial activity and can be used for the treatment of infectious diseases.

The administration of the pharmaceutical formulations of the present invention can be combined with other therapeutic treatments; for example, they can be combined with chemotherapy and radiation therapy of cancer and leukemias, as studies with cultured cells and animal models have demonstrated that curcumin may potentate the anticancer efficacy of chemotherapy and radiation therapy, while protecting normal tissues and cells from treatment-related toxicity.

In the prevention and treatment of diseases and clinical conditions, an effective dose of the cyclodextrin complex of curcumin is administered to the human or animal subject.

Effective doses vary widely depending on the disease and clinical condition, route of administration, and dosage form. The doses are generally 0.1-300 mg/kg/day. Doses in oral administration are generally higher than in parenteral administration, such as 1-300 mg/kg/day. Intravenous and parenteral doses are generally 0.5-100 mg/kg/day. In topical and mucosal administration the doses vary depending on the surface area to be treated, and doses below 0.1 mg/kg/day may be used.

The present invention further provides a method for the protection of organs, tissues and cells during hypothermic and normothermic preservation and perfusion, which comprises contacting the organs and cells with a preservation solution containing a cyclodextrin complex of curcumin. Curcumin protects organs and cells during hypothermic storage and perfusion from ischemia, hypothermic injury and oxidative stress. During rewarming and reperfusion curcumin protects the organs against reperfusion injury. The present invention makes it possible to add curcumin in a stable and water-soluble form to aqueous preservation and perfusion solutions, which is a prerequisite for the exploitation of curcumin's protective effects in the preservation of organs and cells.

Curcumin is efficiently delivered into the organ transplant during intravascular flush with a preservation solution containing the novel curcumin composition, as demonstrated in Example 9.

The present invention is particularly effective in preventing ischemia reperfusion injury in ischemically damaged organ transplants. "Ischemically damaged" means herein organ transplants retrieved from deceased donors, which are typically subjected to warm ischemia before harvesting. Such organs often suffer from severe ischemia reperfusion injury after transplantation, which causes delayed graft function and chronic graft dysfunction. When organs are retrieved after cardiac death, even graft non-function occurs in a considerable proportion of recipients. The efficacy of the present invention to effectively prevent graft non-function and associated mortality, delayed graft function and chronic graft dysfunction has been demonstrated in a porcine kidney transplantation model representing severe reperfusion injury (Example 9). No other compound has so far proven equally protective under corresponding stringent conditions representing organ transplantation from deceased donors.

By definition, "hypothermia" as used herein refers to temperatures below the body temperature, particularly below 35° C. Organ transplants are typically stored between 10° C. and 0° C. Within the scope of the present invention, "hypothermia" also refers to temperatures used in cryopreservation, i.e. preservation of cells and tissues in a frozen or vitrous state at temperatures below 0° C.

According to the present invention, organs for transplantation are flushed with an aqueous solution containing a cyclodextrin complex of curcumin during harvesting. During preservation ex vivo, organs may be continuously perfused or, alternatively, maintained in cold after initial flush with a preservation solution containing the cyclodextrin complex of curcumin. Organs may be flushed before implantation with rinse solutions, such as Ringer's solution, containing the cyclodextrin complex of curcumin. Tissues and cells are immersed in an aqueous solution containing the cyclodextrin complex of curcumin. Organs may also be perfused in situ with blood or a blood-free solution containing the cyclodextrin complex of curcumin, particularly for preservation of the heart during temporary cardiac arrest and heart surgery.

Curcumin concentrations effective in the protection of organs and cells are generally 0.5 to 250 µmol/l, in particular 5-200 µmol/l.

A solution composition, which is added to the preservation, perfusion and storage solutions, contains similar auxiliary substances as the solution for intravenous administration. A powder formulation may be also used, which is reconstituted before use.

The present invention also comprises kits consisting of a first solution or powder formulation containing a cyclodextrin complex of curcumin and a second solution which are combined before use. The complex may be incorporated in medical devices, such as in a bag set used for preparation or treatment of blood cells, where it is can be stored in liquid or solid form and reconstituted before use.

A composition containing the cyclodextrin complex of curcumin can be added to conventional organ preservation and perfusion solutions. Such commercially available preservation solutions are exemplified by ViaSpan® (Bristol-Myers Squibb, N.Y., USA), Celsior® (Genzyme, Mass., USA), KPS-1 and SPS-1 (Organ Recovery Systems, Inc., IL, USA), Perfadex® (Vitrolife AG, Sweden), Custodiol® (Dr. Franz Köhler Chemie GmbH, Germany, and Essential Pharmaceuticals, LLC, PA, USA), SCOT (MacoPharma, France) and Plegisol® (Hospira Inc, IL, USA). Other substances, such as albumin, can be also added.

Methods Used in the Examples:

The concentration of curcumin was measured by reverse phase HPLC (high pressure liquid chromatography). The separation was performed on a 4 μm Nova-Pak C18 column, 150×3.9 mm (Waters, Milford, Mass., USA). The mobile phase was composed of 0.5% citric acid adjusted to pH 3 with potassium hydroxide and acetonitrile (55:45). A flow rate of 1.0 ml/min was used. Absorbance was monitored at 256 nm and 430 nm. 4-Hydroxybenzophenon (Fluka) was used as an internal standard. The retention times of curcumin, demethoxycurcumin and bisdemethoxycurcumin were approximately 7.4, 6.8, and 6.2 min. Tissue samples were homogenized in 20 mmol/l potassium citrate, pH 6.0, 50% acetonitrile, centrifuged (10,000 g) and the clarified supernatant was diluted with the mobile phase before injection. Endotoxins were determined by the gel-clot method and the chromogenic turbidimetric method according to Ph. Eur. 2.6.14.

The following non-limiting examples illustrate the invention:

Example 1

Manufacture of a Water-Soluble Stable Cyclodextrin Complex of Curcumin and a Pharmaceutical Formulation Thereof 2-Hydroxypropyl-γ-cyclodextrin (CAVASOL W8 Pharma, Wacker Chemi, Germany) was dissolved to a concentration of 100 gain 0.2 mol/l sodium hydroxide solution at about 23° C. Curcumin (Curcumin C3 Complex, Sabinsa, N.J., USA) was added to a concentration of 14 g/l. The solution was agitated and protected from light. After complete dissolution of curcumin, the pH was lowered to 6.1 by addition of a mixture of 0.62 mol/l hydrochloric acid and 0.12 mol/l citric acid. The solution was sterile filtered and filled aseptically into sterile vials. The composition of the product is shown in Table 1.

TABLE 1

| Characteristic | Value |
| --- | --- |
| Curcumin | 30 mmol/l (11 g/l) |
| Cyclodextrin | 53 mmol/l (83 g/l) |
| Sodium chloride | 103 mmol/l |
| Sodium citrate buffer | 20 mmol/l |
| pH | 6.1 |
| Calculated osmolarity | 330 mOsmol/l |
| Endotoxins | <1 IU/ml |

Example 2

Comparison of the Cyclodextrin Complex of the Present Invention with Other Cyclodextrin and Gelatin Complexes of Curcumin Complex formation of curcumin with different cyclodextrins, including 2-hydroxypropyl-γ-cyclodextrin (HPγCD), 2-hydroxypropyl-β-cyclodextrin (HPβCD; CAVASOL W7 Pharma, Wacker Chemi), sulfobutylether-β-cyclodextrin (SBEβCD; CyDex, N.J., USA), and γ-cyclodextrin (γCD; Sigma Aldrich, Germany) was compared. First, 100 g/l of HPγCD and HPβCD and 135 g/l of SBEβCD were dissolved in 0.1 mol/l sodium hydroxide, 8.8 g/l of curcumin was added and the solutions were agitated. After complete dissolution of curcumin the pH was lowered to 7.0, and further to pH 5.0 in part of the solution, with 0.5 mol/l citric acid. A 47 g/l solution of γCD was also made in 0.1 mol/l sodium hydroxide, curcumin was added to a concentration of 4.4 g/l and agitated. After dissolution of curcumin, the pH was lowered to 7.0, and further to pH 5.0 in part of the solution, with 0.5 mol/l citric acid. All solutions were clear and intense red at alkaline pH. During lowering of the pH, a considerable amount of yellow precipitate was formed in the other cyclodextrin solutions but not in the HPγCD solution. The precipitation was most extensive in the γCD solution. The other solutions turned orange yellow when pH was lowered below 8, whereas the HPγCD solution was red at pH 7.4. The solutions were sterile filtered and stored at room temperature for 1 week. The properties of the solutions are shown in Table 2.

A 2% gelatin solution (Sigma Aldrich) was adjusted to pH 10 with 1 mol/l sodium hydroxide. Curcumin (C3) was dissolved in 0.1 mol/l sodium hydroxide to a concentration of 9 mg/ml. The curcumin solution was added to the gelatin solution to provide a 5.5% loading of curcumin to gelatin (ratio of weight of curcumin to gelatin, U.S. Pat. No. 4,999,205). A clear red solution was obtained. The pH was decreased to pH 7.0 and further to pH 5.0 in part of the solution with 0.1 mol/l citric acid. A considerable amount of precipitate was formed when the pH was lowered. Yellow solutions were obtained, which were sterile filtered and stored at room temperature for 1 week. The properties of the solution are shown in Table 2.

TABLE 2

| Curcumin complex | | Curcumin | Recovery of |
| --- | --- | --- | --- |
| No. | Complex | pH | (mmol/l) | added curcumin |
| 1 | HPγCD | 5.0 | 21.9 | 100% |
| 2 | HPγCD | 7.0 | 22.3 | 97% |
| 3 | HPβCD | 5.0 | 2.7 | 12% |
| 4 | HPβCD | 7.0 | 3.9 | 17% |
| 5 | SBEβCD | 5.0 | 5.3 | 24% |
| 6 | SBEβCD | 7.0 | 6.0 | 26% |
| 7 | γCD | 5.0 | <0.1 | <1% |
| 8 | γCD | 7.0 | <0.1 | <1% |
| 9 | Gelatin | 5.0 | 1.3 | 54% |
| 10 | Gelatin | 7.0 | 1.2 | 48% |

Example 3

Stability of the Cyclodextrin Complex of Curcumin

Curcumin complexes with HPγCD were made by dissolving different amounts of HPγCD in 0.1 mol/l sodium hydroxide and adding different amounts of curcumin, thus giving different cyclodextrin/curcumin (CD/C) ratios. After dissolution of curcumin, the pH was lowered to different pH values with 0.5 mol/l citric acid. The solutions were sterile filtered, filled aseptically into vials and stored at room temperature protected from light. Curcumin concentration was determined by HPLC at the time points indicated in Table 3.

TABLE 3

| Formulation | | | Curcumin concentration (mmol/l) after storage at room temperature | | |
| --- | --- | --- | --- | --- | --- |
| No | CD/C ratio | pH | Initial | 1 week | 3 months |
| 1 | 2.7 | 7.4 | 21.6 | 21.6 | 21.3 |
| 2 | 2.7 | 7.0 | 22.3 | 22.1 | 21.4 |
| 3 | 2.8 | 6.0 | 21.3 | 22.8 | 21.9 |

TABLE 3-continued

| Formulation | | | Curcumin concentration (mmol/l) after storage at room temperature | | |
|---|---|---|---|---|---|
| No | CD/C ratio | pH | Initial | 1 week | 3 months |
| 4 | 3.0 | 5.0 | 21.9 | 21.7 | 21.5 |
| 5 | 3.6 | 6.9 | 11.3 | 10.6 | 10.6* |
| 6 | 2.8 | 6.9 | 11.0 | 11.4 | 10.0* |
| 7 | 2.0 | 6.9 | 10.2 | 10.4 | 10.2* |
| 8 | 1.5 | 6.9 | 10.1 | 9.8 | 9.5* |

*Storage time 2 months

Example 4

Manufacture of a Cyclodextrin Complex of Curcumin and a Pharmaceutical Formulation Thereof Containing 20 g/l Curcumin 2-Hydroxypropyl-γ-cyclodextrin was dissolved to a concentration of 205 g/l in 0.2 mol/l sodium hydroxide solution. Curcumin was added to a concentration of 25 g/l. The solution was agitated and protected from light. After complete dissolution of curcumin, the pH was lowered to 6.1 by addition of a mixture of 0.62 mol/l hydrochloric acid and 0.12 mol/l citric acid. The solution was sterile filtered and filled aseptically into sterile vials. The composition of the product is shown in Table 4.

TABLE 4

| Characteristic | Value |
|---|---|
| Curcumin | 53 mmol/l (20 g/l) |
| Cyclodextrin | 110 mmol/l (171 g/l) |
| Sodium chloride | 96 mmol/l |
| Sodium citrate buffer | 19 mmol/l |
| pH | 6.1 |
| Calculated osmolarity | 367 mOsmol/l |

Example 5

Comparison of the Present Cyclodextrin Complex of Curcumin with a Complex Formed without the Alkaline Dissolution Step Hydroxypropyl-γ-cyclodextrin (135 g/l) was dissolved in water for injection, the solution was filtered through a positively charged membrane filter, and 1 mol/l sodium hydroxide was added to 0.18 mol/l concentration. Curcumin C3 powder was added to 15 g/l, the solution was agitated and after dissolution of curcumin, pH was adjusted to pH 6.0 with a mixture of 0.6 mol/l hydrochloric acid and 0.12 mol/l citric acid. The solution was sterile filtered, filled aseptically into glass vials, capped and sealed. Curcumin concentration in the solution was 34 mmol/l. A comparator complex was prepared by dissolving molar excess of curcumin (25 g/l) in 100 g/l hydroxypropyl-γ-cyclodextrin in 20 mmol/l sodium citrate buffer, pH 6.0. After mixing for 5 days, the solid material was removed by particle filtration and the solution was sterile filtered. Curcumin concentration was 0.5 mmol/l. The proportions of curcuminoids and cyclodextrin/curcumin ratio in the compositions are shown in Table 5. Curcumin C3 powder containing curcumin, demethoxycurcumin (DMC) and bis-demethoxycurcumin (BDMC) was dissolved in dimethyl sulfoxide.

TABLE 5

| Composition | Proportion of curcuminoids (%) | | | Cyclodextrin/curcumin ratio |
|---|---|---|---|---|
| | Curcumin | DMC | BDMC | |
| Curcumin C3 powder | 79.9 ± 1.2 | 16.4 ± 0.5 | 3.2 ± 0.3 | |
| Present complex | 80.4 ± 0.8 | 16.6 ± 0.2 | 2.8 ± 0.4 | 1.7 |
| Comparator complex | 54.2 ± 0.6 | 14.0 ± 0.3 | 31.8 ± 0.9 | 68.1 |

Curcumin in the present composition remained stable for 2 years at 2-8° C. After 2 years at 21-25° C. the drop in curcumin concentration was on average 15%. In photostability studies, more than 95% of curcumin in the present composition was stable during illumination of the solution with high intensity mercury lamp (200-600 nm, Heraeus TQ150) for 16 h, whereas curcumin dissolved in methanol (4 mmol/l) decomposed with a half-life of 65 min under the same conditions. As reported before (2,4), a cyclodextrin complex of curcumin prepared without the alkaline dissolution step was even less stable than curcumin in methanol during illumination.

Example 6

Efficient Delivery of Curcumin into the Lungs and Prevention of Lung Injury by Nebulization of the Present Composition The present solution composition containing 34 mmol/l curcumin (Experiment 5) was given to mice by nebulization in a whole-body dosing chamber for 20 min. Aerosol was generated by a micropump nebulizer fitted at the inlet of the chamber. In some experiments 50 μl of the solution composition was administered through an intratracheal catheter to anesthetized mice. Acute lung injury was induced by intratracheal instillation of 50 μl of endotoxin in saline before nebulization. Lung fibrosis was induced by intratracheal administration of 50 μl bleomycin sulfate in saline. Lavage fluid samples were analyzed for intra-alveolar neutrophil infiltration by hemocytometer and differential cytology and pulmonary fibrosis was assessed by hydroxyproline determination of lung homogenates according to published procedures.

Nebulization of the present solution composition effectively prevented intra-alveolar neutrophil infiltration induced by endotoxin, which indicated that effective doses of curcumin were delivered into the lungs. Repeated pulmonary dosing of the solution composition significantly reduced pulmonary fibrosis induced by bleomycin. The solution was well tolerated even in intratracheal administration.

Example 7

Effective Delivery of Curcumin into Bladder Urothelium after Intravesical Instillation of the Present Composition Female rats were anesthetized and a catheter was passed through the urethra into their bladder. The present solution composition was diluted with 0.9% sodium chloride to curcumin concentrations of 100 μmol/l and 400 μmol/l, and 250 μl of the solution was instilled into the bladder. After 1 hour the bladders were emptied. The animals were euthanized after different time periods and the bladder wall was used for snap-freezing and sectioning to visualize curcumin by fluorescence microscopy (FITC filter) and determination of curcumin by HPLC. Curcumin fluorescence was evenly distributed into the entire urothelium and persisted at least up to 24 hours. In the healthy bladder wall the distribution of curcumin into deeper layers was prevented by the intact basement membrane, whereas in urothelial cancer the basement membrane becomes destroyed allowing effective distribution of curcumin into the entire cancer tissue. No toxicity was observed in the histological examination of the bladder wall of healthy animals 24 hours after the intravesical instillation.

Example 8

Effective Delivery of Curcumin into Brain Tissue after Intranasal Administration of the Present Composition Rats were anesthetized and placed on their back. 50 µl of the present solution composition containing 34 mmol/l curcumin was applied intranasally. After 30 min the rats were killed and the brain was removed from the skull. Different anatomical regions were dissected and snap-frozen for curcumin determination by HPLC. Curcumin concentration in the different areas of the brain cortex was 17-47 nmol/g. Highest levels (22-79 nmol/g) were measured in the olfactory bulbs. No curcumin could be measured in the brain tissue after intravascular administration of up to 50 mg/kg of curcumin. These experiments indicated that curcumin is efficiently delivered by the present composition through the olfactory epithelium into the brain, bypassing the blood-brain barrier.

Example 9

Effective Delivery of Curcumin into Kidney Transplants and Protection Against Reperfusion Injury by the Addition of the Present Composition into Preservation Fluid 1 ml of the present solution composition containing 34 mmol/l curcumin was added to 500 ml of preservation solution (Custodiol) and used for intra-arterial flushing of pig kidneys ex vivo. About 80% of curcumin added to the preservation fluid was delivered into the kidney tissue during the flush. Curcumin concentration in kidney biopsies after the flush was on average 180 nmol/g.

The protective effect of the present composition was studied in a porcine kidney transplantation model, in which the left kidney is removed and subjected to 60 min of warm ischemia, flushed with 500 ml of cold UW solution (Viaspan) and preserved in cold for 24 hours before autotransplantation. The contralateral kidney is removed. Control and treatment groups were treated similarly otherwise but in the treatment group the present solution composition was added to UW solution (1 ml per 500 ml) before the flush of the kidney.

Kidney function was effectively restored in the treatment group as indicated by normalization of serum creatinine levels but remained severely impaired in the controls during the follow-up for 3 months (Table 6). The survival of the animals in the treatment group was remarkably better than in the control group (83% vs. 29%, p<0.05). Mortality was caused by kidney non-function. Renal histology three months after transplantation was close to normal in the treatment group, while there was extensive interstitial fibrosis in controls (fibrosis score 7.1±0.5% vs. 37.3±2.8%, p<0.05). The treatment group secreted only little protein into urine, whereas the control group had severe proteinuria (0.29±0.15 g/24 hour vs. 3.76±0.82 g/24 hour).

TABLE 6

| Time after | Serum creatinine (µmol/l; mean ± SD) | |
|---|---|---|
| transplantation | Treatment group (n = 6) | Control group (n = 7) |
| 7 days | 555 ± 130 | 1763 ± 570 |
| 30 days | 196 ± 44 | 1069 ± 870 |
| 90 days | 93 ± 7 | 435 ± 67 |

REFERENCES

1. Anand P, Kunnumakkara A B, Newman R A, Aggarwal B B. Bioavailability of curcumin: problems and promises. Mol. Pharm. 2007; 4:807-18.
2. Tønnesen H H, Másson M, Loftsson T. Studies of curcumin and curcuminoids. XXVII. Cyclodextrin complexation: solubility, chemical and photochemical stability. Int J. Pharm. 2002; 244:127-35.
3. Baglole K N, Boland B G, Wagner B D. Fluorescence enhancement of curcumin upon inclusion into parent and modified cyclodextrins. J Photochem Photobiol A. 2005; 173:230-7.
4. Tomren M A, Másson M, Loftsson T, Tønnesen H H. Studies on curcumin and curcuminoids XXXI. Symmetric and asymmetric curcuminoids: stability, activity and complexation with cyclodextrin. Int J. Pharm. 2007; 338:27-34.
5. Chen C, Johnston T D, Wu G, Ranjan D. Curcumin has potent liver preservation properties in an isolated perfusion model. Transplantation 2006; 82:931-7.
6. Tønnesen H H, Karlsen J. Studies on curcumin and curcuminoids. VI. Kinetics of curcumin degradation in aqueous solution. Z Lebensm Unters Forsch. 1985; 180:402-4.
7. American Thoracic Society/European Respiratory Society International Multidisciplinary Consensus Classification of the Idiopathic Interstitial Pneumonias. Am J Respir Crit. Care Med. 2002, 165, 277-304.

The invention claimed is:
1. A method of producing a water-soluble complex of curcumin with an alkyl or ether derivative of gamma-cyclodextrin comprising:
   a) contacting curcumin with the gamma-cyclodextrin derivative at a molar ratio of about 1:1 to 1:6 in an aqueous phase at a pH of at least 11 to form a solution, and
   b) lowering the pH of the solution to below pH 8, whereby a stable cyclodextrin complex of curcumin is formed in said aqueous phase.
2. The method according to claim 1, wherein the pH of the solution is lowered to a value in the range from about 3 to below 8.
3. The method according to claim 1, comprising recovering the solution obtained containing a cyclodextrin complex of curcumin.
4. The method according to claim 3, wherein the solution recovered exhibits a red color at pH 7.4.
5. A method of manufacturing an endotoxin-free cyclodextrin complex of curcumin comprising:
   a) contacting curcumin with the cyclodextrin in an aqueous phase at a pH of at least 11 to form a solution of curcumin and cyclodextrin,
   b) lowering the pH of said solution to below pH 8, and c) recovering the solution thus obtained containing an endotoxin-free cyclodextrin complex of curcumin.

6. The method according to claim 1, wherein the pH of the solution is lowered to a value in the range of from about 4.0 to 7.6.

* * * * *